US00PP34244P2

(12) United States Plant Patent
Zlesak

(10) Patent No.: US PP34,244 P2
(45) Date of Patent: May 17, 2022

(54) ***PHYSOCARPUS* PLANT NAMED 'ZLENATALIE'**

(50) Latin Name: *Physocarpus opulifolius*
Varietal Denomination: ZLENatalie

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 0 days.

(21) Appl. No.: 17/300,972

(22) Filed: Jan. 4, 2022

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 6/74; A01H 5/02
See application file for complete search history.

*Primary Examiner* — Keith O. Robinson

(57) ABSTRACT

'ZLENatalie' is a new and distinct cultivar of *Physocarpus opulifolius* plant having an upright, mounded, dense plant habit; compact overall plant size; strong branching characteristics; small orange-red to golden emerging foliage that matures to purple; short internode length; resistance to powdery mildew; corymbs of small blush-white flowers that are produced in late spring into early summer and to a limited extent again on some current season terminals in mid-summer into fall; coral-pink to red follicle color when in full sun for about a month after fertilization; and ability to root and grow vigorously from softwood and semi-hardwood stem cuttings.

6 Drawing Sheets

Latin name of the plant claimed: *Physocarpus opulifolius*. Variety denomination: 'ZLENatalie'.

BACKGROUND OF THE INVENTION

The present invention relates to a new and distinct cultivar of *Physocarpus opulifolius* and will be referred to hereafter by its cultivar name, 'ZLENatalie'. *Physocarpus opulifolius* (commonly known as ninebark, common ninebark, Atlantic ninebark, and Eastern ninebark) is a deciduous shrub grown for landscape use. The key objective within the *Physocarpus opulifolius* breeding program I initiated in St. Paul, Minn. in 2001 and now continue in River Falls, Wis. has been to develop new *Physocarpus opulifolius* cultivars that are compact growing, well-branched, healthy, and possess colorful foliage. One specific goal has been to develop a cultivar with the orange-red to golden new foliage color that matures to purple of *Physocarpus opulifolius* 'Center Glow' (disclosed in U.S. Plant Pat. No. 16,894) and the compact, well-branched growth habit and small foliage of cultivars such as *Physocarpus opulifolius* var. *nanus* (not patented) and its descendant *Physocarpus opulifolius* 'Donna May' (disclosed in U.S. Plant Pat. No. 22,634).

'ZLENatalie' originated as a unique seedling within an $F_2$ population that was developed by open-pollination of twelve $F_1$ seedlings (growing in isolation) from the cross *Physocarpus opulifolius* 'Donna May' as the female parent and *Physocarpus opulifolius* 'Dart's Gold' (not patented) as the male parent. Ninebark displays self-incompatibility, and it is expected that the developing seeds were from crosses between compatible siblings. Seeds were harvested and bulked together from the $F_1$ seedlings. Pollination that led to this $F_2$ population of seedlings from which 'ZLENatalie' was identified occurred in June 2014. The seeds of this population germinated during the winter of 2014/2015 indoors under florescent lights in St. Paul, Minn. At the end of the first growing season, seedlings with attractive foliage color, relatively compact growth habit, and powdery mildew resistance were retained. 'ZLENatalie' stood out as a highly desirable genotype among this seedling population and was transplanted to a larger container in 2016. 'ZLENatalie' was first asexually propagated using semi-hardwood and softwood stem cuttings in 2016. I have found that the characteristics of 'ZLENatalie' are stable and true to type over successive generations of vegetative propagation.

'ZLENatalie' was unique relative to other ninebark seedlings in my breeding program and all cultivars I am aware of because of its warm orange-red to golden new growth that matures to purple and its compact and very well-branched plant habit. 'ZLENatalie' first flowered in 2017. It has attractive blush-white flowers that are abundant and attractive against the colorful foliage. As follicles develop, they are a coral-pink to red color for about a month and provide additional ornamental value. 'ZLENatalie' displays a modest degree of repeat flowering later in the growing season on the terminals of current season's stems. Natural branching without pruning leads to an abundance of new stems with colorful tips and adds to the ornamental value of 'ZLENatalie'.

SUMMARY OF THE INVENTION

The primary objective of the breeding goal was substantially achieved, along with other desirable improvements, as evidenced by the following unique combination of characteristics that are outstanding in the new variety and that distinguish it from other ninebark in my breeding program as well as from all other cultivars of *Physocarpus opulifolius* of which I am aware:

1. Upright, mounded, dense plant habit;
2. Compact overall plant size;
3. Strong branching characteristics;
4. Small orange-red to golden emerging foliage that matures to purple;
5. Short internode length;
6. Resistance to powdery mildew;
7. Corymbs of small blush-white flowers that are produced in late spring into early summer and to a limited extent again on some current season terminals in mid-summer into fall;
8. Coral-pink to red follicle color when in full sun for about a month after fertilization;
9. Ability to root and grow vigorously from softwood and semi-hardwood stem cuttings.

Asexual reproduction of this new cultivar by rooting of softwood and semi-hardwood cuttings, as performed at River Falls, Wis. and Cottage Grove, Minn. shows that the foregoing and all other characteristics and distinctions come true to form and are established and transmitted through succeeding asexual propagations.

COMPARISON WITH PARENTS

'ZLENatalie' is a seedling in the $F_2$ generation from a cross of 'Donna May' and 'Dart's Gold' and combines features of both cultivars. 'ZLENatalie' is similar to 'Donna May' in that leaves mature to purple. New growth of 'ZLENatalie' has a warm orange-red to golden color before it matures to purple, while 'Donna May' has greenish-purple new growth before it matures to purple. Both 'ZLENatalie' and 'Donna May' have similar plant and foliage size along with abundant branching. 'ZLENatalie' reliably has some rebloom later in the growing season on terminals of vigorous new stems. 'Donna May' can rebloom later in the growing season, but does so less reliably and less abundantly.

'ZLENatalie' differs from 'Dart's Gold' in that 'ZLENatalie' has smaller leaves, smaller flowers, smaller fruit, shorter internodes, and an overall smaller plant size and it is more densely branched than 'Dart's Gold'. The foliage of 'ZLENatalie' is a warm orange-red to golden color that matures to purple, whereas the foliage color of 'Dart's Gold' is yellow-green. The flowers of 'ZLENatalie' have more pink in them and the developing follicles are more richly pigmented with a coral-pink to red during development than 'Dart's Gold'. 'ZLENatalie' reliably has some rebloom later in the growing season, and I have not observed reliable rebloom on 'Dart's Gold'. The greatest similarity between 'ZLENatalie' and 'Dart's Gold' is that both have brightly colored new growth ('ZLENatalie' has orange-red to golden new growth and 'Dart's Gold' has yellow-green to golden new growth).

COMPARISON OF 'ZLENATALIE' WITH SIMILAR CULTIVAR

The *Physocarpus opulifolius* cultivar that shares the greatest similarity with 'ZLENatalie' is 'Center Glow'. New growth of both cultivars is a warm orange-red to golden color that matures to purple. 'ZLENatalie' has smaller leaves, smaller flowers, a smaller mature plant size, and more abundant branching than 'Center Glow'. 'ZLENatalie' modestly reblooms in mid-summer into fall, while 'Center Glow' does not typically rebloom.

BRIEF DESCRIPTION OF THE DRAWINGS

The accompanying colored photographs illustrate key features of 'ZLENatalie'. Photographs show the colors as true as it is reasonably possible to obtain with colored reproductions of this type. Colors in the photographs may differ slightly from the color values cited in the detailed botanical description, which accurately describe the colors of 'ZLENatalie'.

DETAILED BOTANICAL DESCRIPTION

Figure 1:
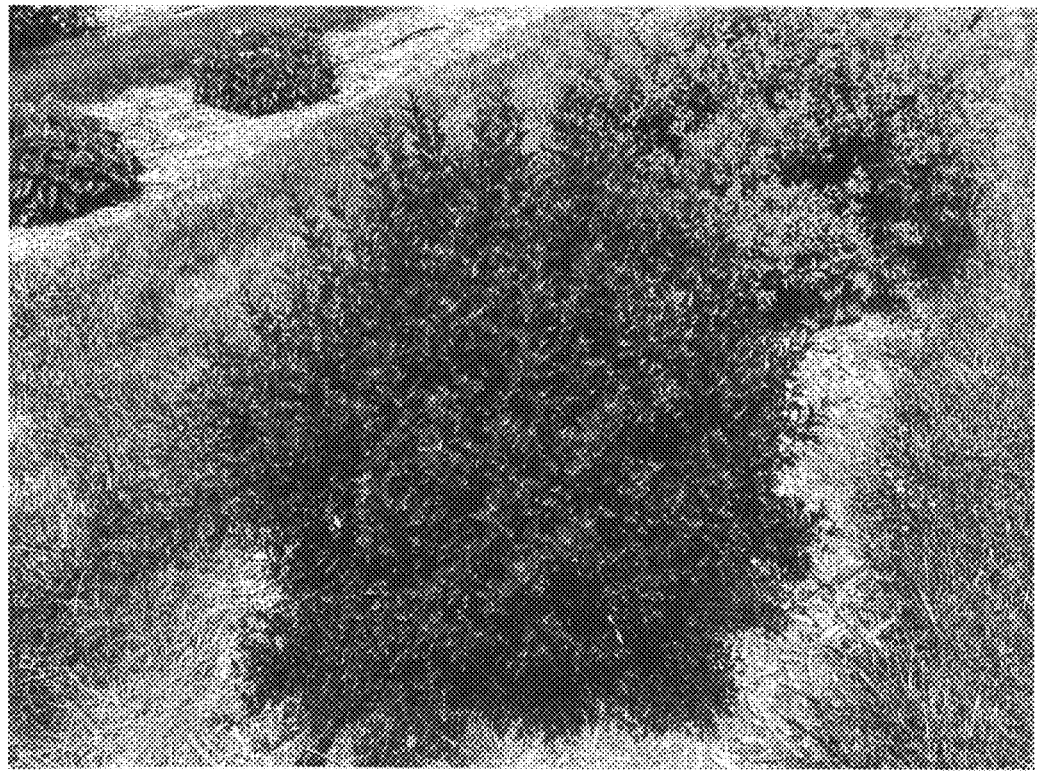
FIG. 1 illustrates a five-year-old plant of 'ZLENatalie' summer 2021.
Figure 2:
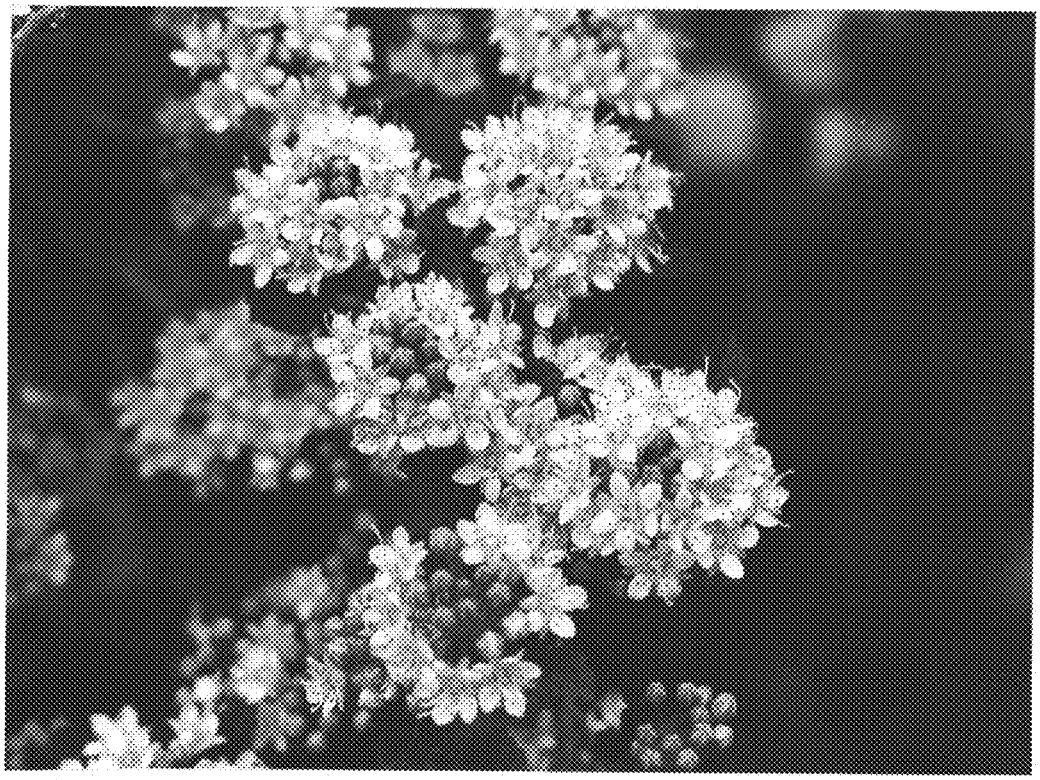
FIG. 2 illustrates corymbs of 'ZLENatalie' flowers at different stages of opening in mid-June 2021.
Figure 3:
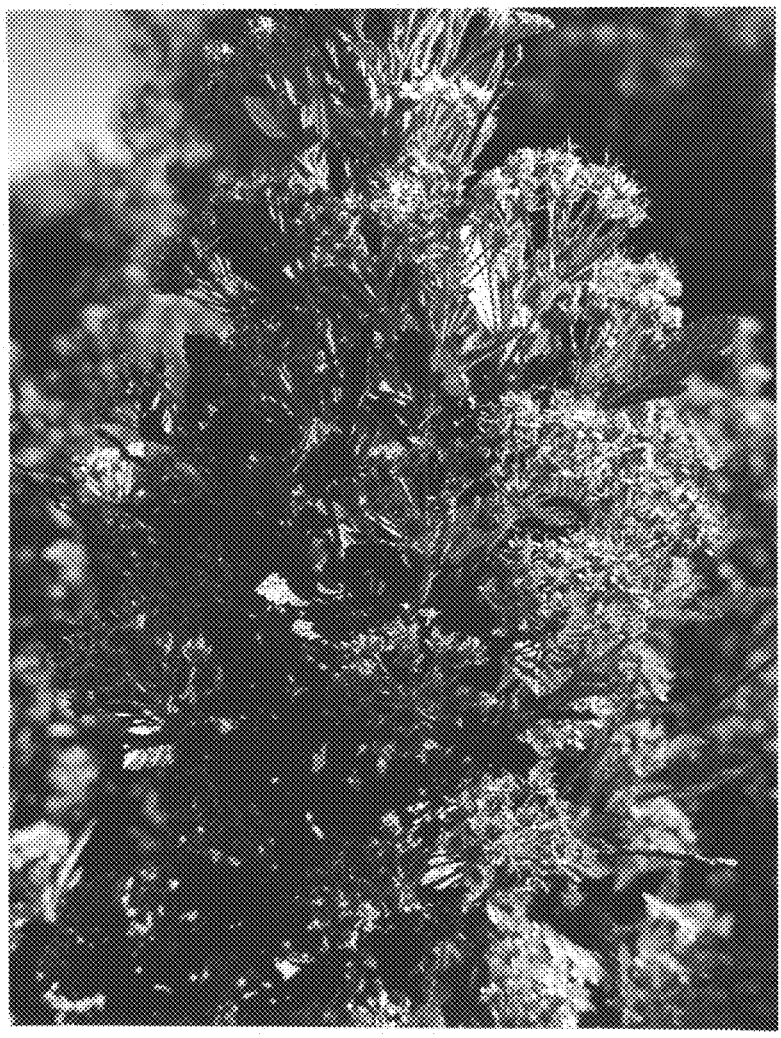
FIG. 3 illustrates developing follicles of 'ZLENatalie' in early July 2021.
Figure 4:
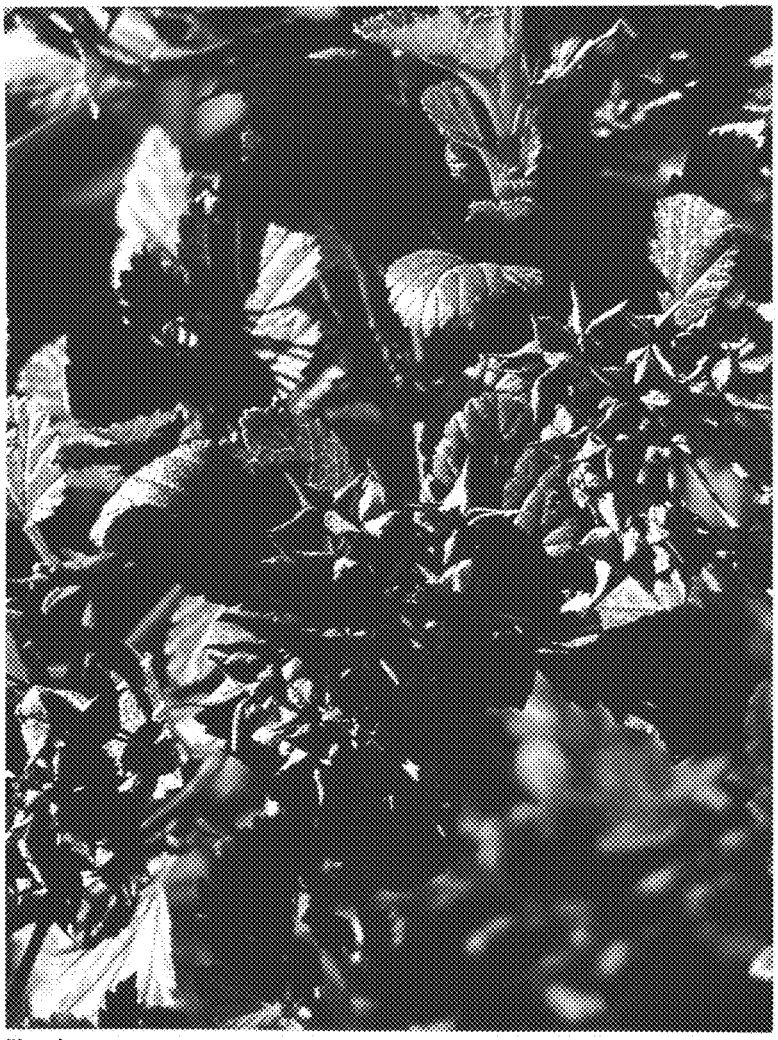
FIG. 4 illustrates mature follicles of 'ZLENatalie' opening September 2021.
Figure 5:
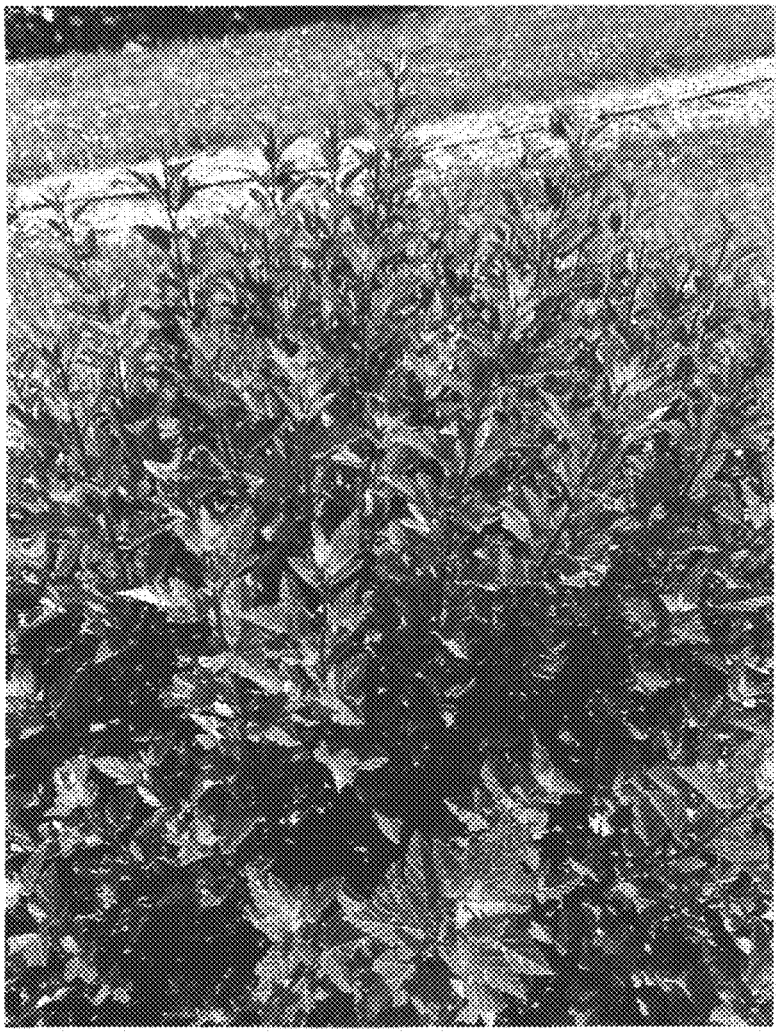
FIG. 5 illustrates emerging golden foliage of 'ZLENatalie' that becomes purple as it ages in the sun.
Figure 6:
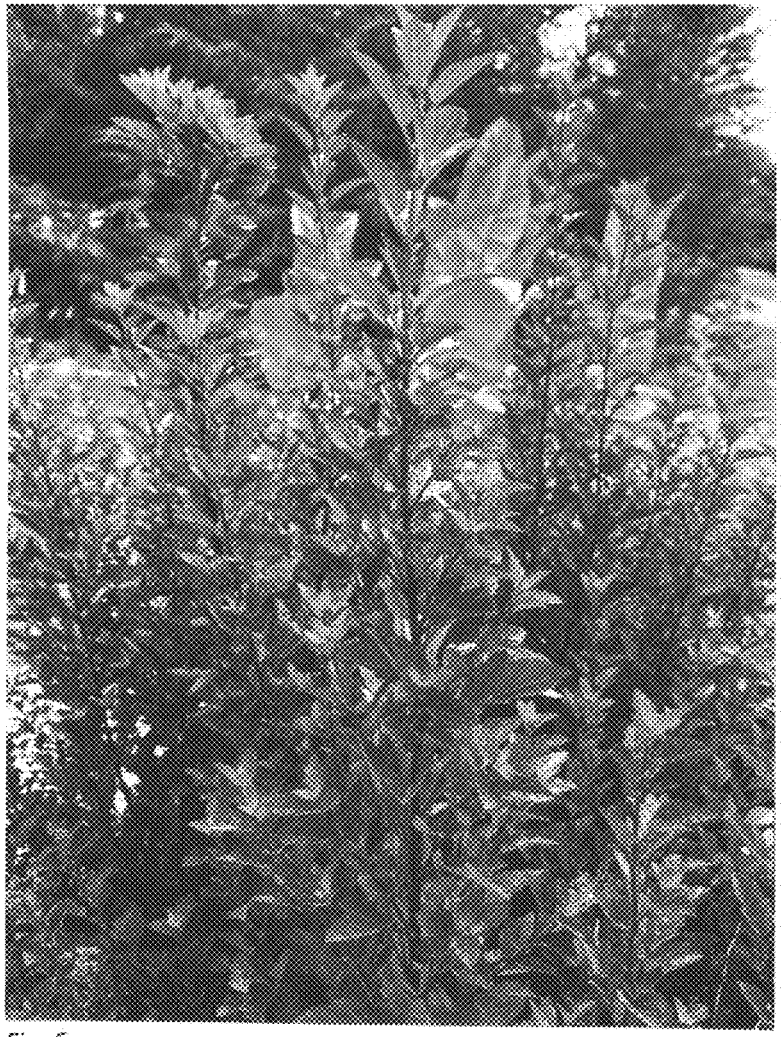
FIG. 6 illustrates abundant natural branching on a current season stem of 'ZLENatalie' without pruning and emerging orange-red foliage that becomes purple with age.
Figure 7:
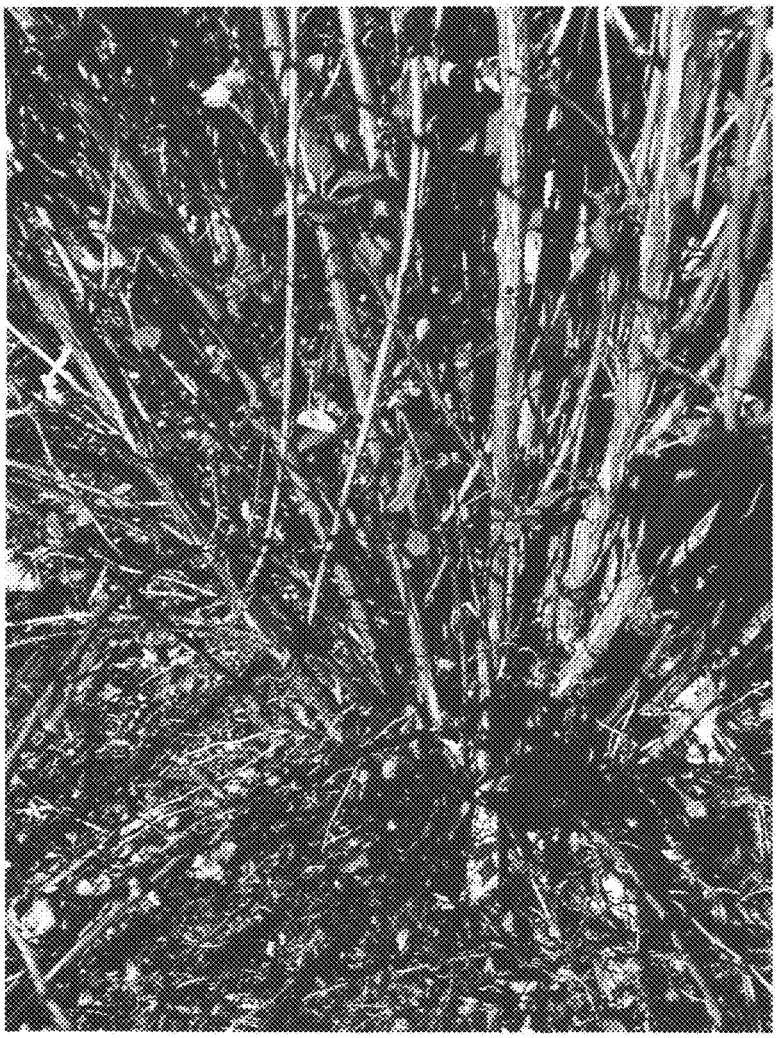
FIG. 7 illustrates the oldest stems at the base of a plant in its fifth growing season of 'ZLENatalie'.

The following is a detailed description of 'ZLENatalie', the new *Physocarpus opulifolius* cultivar, with color descriptions using terminology in accordance with The Royal Horticultural Society (London) Colour Chart (2015), except where ordinary dictionary significance of color is indicated. The phenotype of the new cultivar may vary with variations in environmental, climatic, and cultural conditions, as it has not been tested under all possible environmental conditions. Descriptions are based on observations of plants that are at least four-years-old growing in River Falls, Wis. and Cottage Grove, Minn. during the 2021 growing season.

Classification:

*Botanical.*—*Physocarpus opulifolius* 'ZLENatalie'.

*Common names of the species.*—Ninebark, common ninebark, Atlantic ninebark, and Eastern ninebark.

*Commercial.*—Deciduous shrub.

Parentage:

*Origin.*—Seedling from within an $F_2$ population of a cross of *Physocarpus opulifolius* 'Donna May' and *Physocarpus opulifolius* 'Dart's Gold'.

General description:

*Plant habit.*—Upright, mounded, and compact.

*Plant size.*—1.0-1.2 m in overall height and width.

*Growth habit.*—Vigorous and dense with abundant branching.

*Blooming period.*—About 21 days from mid-June to early July. Plants can have modest rebloom on the terminals of vigorous new stems from mid-August into October.

*Hardiness.*—Cold hardy to at least USDA Zone 4.

*Root description.*—Fibrous and vigorous.

*Diseases and pest resistance.*—'ZLENatalie' has shown well above average resistance to powdery mildew with other ninebark genotypes heavily infected with powdery mildew growing adjacent to it. There are multiple species of fungi that cause powdery mildew on ninebark, and it is unclear which species of fungi were infecting it and the adjacent, more susceptible ninebark genotypes.

*Cultural requirements*.—'ZLENatalie' does well in full to partial sun and well-drained, moderately fertile soil.

Growth and propagation:

*Propagation*.—Softwood and semi-hardwood stem cuttings have been effective.

*Time required for root initiation and initial development*.—It takes about 3 to 4 weeks during the summer using intermittent mist in the greenhouse without supplemental lighting for cuttings to typically form visible roots.

*Time required to obtain a well-rooted cutting*.—It takes about 6 to 7 weeks to produce a well-rooted cutting in a 2-inch container.

Branch description:

*Branch color*.—The background color of current season stems is Yellow-Green Group N144D and in sun it has a Greyed-Red Group 178B overlay. The most mature stems on a six-year-old plant had a mixture of colors on the exfoliating bark; color was primarily Greyed-Orange Group 165C, but there were also areas of Greyed-Orange Group 165B, Greyed-Orange Group 165C, Greyed-Orange Group 165D, and Orange-White Group 158A.

*Branch size*.—Branches produced during the current season of growth ranged from approximately 10-60 cm in length and 1-4 mm in width. The oldest branches on a six-year plant were up to 1.5 cm in diameter at the base of the plant.

*Branch surface*.—Young stems: Glabrous with a slight sheen. Older stems: Exfoliating bark layers that are somewhat dull and no longer have a sheen.

*Internode length*.—1.0-2.0 cm.

*Branch habit*.—Vigorous current season's stems typically produce new stems from axillary buds without pruning. Many vigorous growing stems terminate in a second flush of flowers by mid to late summer (August and September) and this stimulates additional axillary buds on current season's growth to develop into shoots. The angle between the new stems arising from axillary buds and the stem from which they originated is typically 15-50°.

Foliage description:

*Overall leaf size*.—Leaf length is 3.5-5.5 cm and leaf width is 2.0-3.0 cm.

*Leaf division*.—Simple.

*Leaf attachment*.—Petiolate.

*Leaf arrangement*.—Alternate.

*Leaf number*.—It varies, but an actively growing branch can easily produce 30-60 leaves in a growing season.

*Leaf blade shape*.—Ovate in overall leaf blade outline with three prominent lobes.

*Leaf blade base*.—Rounded.

*Leaf blade apex*.—Acute to cuneate.

*Leaf blade venation*.—Primary venation is palmate with three principal veins. The principal veins diverge at the juncture of the leaf blade and petiole and continue with one through the middle of each of the three lobes. Secondary venation off the three principal veins is pinnate.

*Leaf blade margin*.—The three primary lobes have secondary lobes or serrations. The margin on the three primary lobes is best described as doubly serrate. The serrations extend out from the edge of the main leaf blade about 1.0-1.5 mm and there is typically between 3-4 mm between the tips of primary serrations and 1-2 mm between the tips of secondary serrations.

*Leaf blade surface*.—Glabrous on upper and lower surfaces.

*Leaf blade size*.—The leaf blade is approximately 2.5-3.0 cm long and 1.75-2.0 cm wide.

*Leaf blade color*.—Young emerging leaf blades on both surfaces are Yellow-Green Group 150A and have Greyed-Orange Group 176B along the margins. Young recently expanded leaf blades are closest to Greyed-Purple Group 187A on the upper surface and Yellow-Green Group 146C on the lower surface, except the veins on the lower surface are Yellow-Green Group 144C. Mature leaves are Green Group NN137B on the upper surface and Yellow-Green Group 144A throughout the lower surface, except the veins on the lower surface are Yellow-Green Group 144C.

*Petiole size*.—About 0.75-2.0 cm in length and about 1 mm in width.

*Petiole shape*.—Sulcate. The petiole is generally round except for a longitudinal furrow running the length of the upper surface.

*Petiole color*.—Greyed-Red Group 178B on the upper side and Yellow-Green Group 144C on the lower surface.

*Petiole texture*.—Glabrous.

*Stipule number*.—There are two stipules at each node with one on each side of the, leaf petiole.

*Stipule size*.—2-3 mm long and 1.25 mm wide.

*Stipule shape*.—Generally lanceolate.

*Stipule color*.—Greyed-Purple Group 183B on the upper and lower surfaces.

Flower description:

*Inflorescence type*.—A corymb with 15-25 rotate flowers arranged in a hemisphere.

*Inflorescence size*.—Typically 1.5-2.0 cm in height and width.

*Inflorescence lastingness*.—The corymb has open flowers typically for up to 21 days with each individual flower open for approximately 3 days.

*Flower bud shape*.—Elliptic.

*Flower bud size and proportions*.—2.0-2.5 mm in length and 2.0-2.5 mm in width. The receptacle of the bud accounts for about half of the proximal end and the calyx accounts for about half of the distal end of an unopened flower bud.

*Flower bud color*.—The overall color of the unopened buds can best be described as Yellow-Green Group 144D with highlights or an overlay of Orange-Red Group N34C.

*Flower size when fully open*.—5.0-6.0 mm in diameter and 2.0-3.0 mm in depth (not including pedicel).

*Flower symmetry*.—Actinomorphic.

*Flower fragrance*.—Slight and sweet.

*Petal number*.—5.

*Petal size*.—2.5-3.0 mm in length and 2.0-2.25 mm in width.

*Petal shape*.—Elliptic to obovate.

*Petal color*.—As the flowers open, the lower petal surface as the sepals separate is Red-Purple Group 62D. Expanding petals are White Group N155C on the upper surface and White Group N155B on the lower surface. Fully expanded petals are White Group N155B on both the upper and lower surfaces. Aging petals are typically White Group N155D, but can develop a soft pink color close to Red Group 49D right before petal drop.

*Sepal number*.—5.

*Sepal size*.—Length is 3.0 mm and width is 1.5-2.0 mm.

*Sepal shape*.—Deltoid.

*Sepal color*.—Yellow-Green Group N144D with an overlay of Orange-Red Group N34C.

*Sepal texture*.—Hoary on both surfaces.

*Pedicel size*.—The length ranges from about 1.0 cm for the flowers coming from the proximal or lower end of the corymb to about 0.5 cm for the flowers nearest the terminal or center of the corymb. Pedicels are round in cross section and are about 0.75-1.0 mm in diameter.

*Pedicel color*.—Yellow-Green Group 144D with highlights of Orange Red Group N34C. This color is the result of a green base color overlaid with red.

*Pedicel and receptacle texture*.—Glabrous.

*Subtending bract size*.—There is a subtending bract where each pedicel meets the peduncle of the corymb. The subtending bract is 2.0-3.0 mm long and 1 mm wide below where the pedicels attach at the proximal end of the corymb to 1.0-2.5 mm long and 0.75-1.0 mm wide under the more distal pedicels at the terminal or top of the corymb.

*Subtending bract shape*.—Elliptic to obovate with typically 3-5 very small and irregular serrations.

*Subtending bract color*.—Yellow-Green Group 144D with an overlay of Orange-Red Group N34A.

Gynoecium:

*Pistil number per flower*.—Typically there are 4, but sometimes 3.

*Stigma shape*.—Globular.

*Stigma size*.—0.25 mm in height and width.

*Stigma color*.—Yellow Green Group 150B.

*Style shape*.—Linear.

*Style size*.—About 3.0-4.0 mm long and 0.2 mm wide.

*Style color*.—Yellow Group 145D.

*Ovary shape*.—Elliptic.

*Ovary size*.—About 2.0 mm in height and 0.75 mm in width.

*Ovary color*.—Yellow Green Group 145C with Orange-Red Group N34C highlights, especially when exposed to direct sunlight.

Androecium:

*Stamen number per flower*.—Approximately 25.

*Anther shape*.—Elliptic to round.

*Anther size*.—About 0.4 mm in height and width.

*Anther color*.—Black Group 202A.

*Pollen color*.—White Group NN155A.

*Pollen abundance*.—Moderate.

*Filament shape*.—Linear.

*Filament size*.—1.0-3.0 mm long and 0.1-0.2 mm wide.

*Filament color*.—White Group NN155B.

Fruit and seeds:

*Fruit*.—There are typically three or four firm-walled follicles that form per flower. Follicles split along both sides of the seam, but split more readily along the inner or adaxial seam. Follicles are elongated and generally ovate in shape with acuminate tips. They are up to 6.0 mm long and approximately 2.0 mm wide at their widest point. They range in color from Greyed-Purple Group 183C to Greyed-Green Group 193A. Follicle color tends to be green when out of direct sunlight and increasingly red the more direct sunlight that is received. Once mature, follicles dry and turn Greyed-Orange Group 165A.

*Seeds per follicle*.—There are typically 1-2 seeds per follicle.

*Seed shape*.—Ovate.

*Seed size*.—Generally 1.5 mm long and 1.25 mm wide.

*Seed color*.—Mature seed color is between Greyed-Orange Group 164C and Greyed-Orange Group 165D.

Winter hardiness: Acclimated plants of 'ZLENatalie' have displayed strong stem survival (complete survival to minor tip dieback) in United States Department of Agriculture cold hardiness zone 4 without insulation.

I claim:

1. A new and distinct cultivar of *Physocarpus opulifolius* plant named 'ZLENatalie', substantially as herein shown and described, characterized particularly by an upright, mounded, dense plant habit; compact overall plant size; strong branching characteristics; small orange-red to golden emerging foliage that matures to purple; short internode length; resistance to powdery mildew; corymbs of small blush-white flowers that are produced in late spring into early summer and to a limited extent again on some current season terminals in mid-summer into fall; coral-pink to red follicle color when in full sun for about a month after fertilization; and ability to root and grow vigorously from softwood and semi-hardwood stem cuttings.

* * * * *